US00PP29770P2

(12) United States Plant Patent
Lee

(10) Patent No.: US PP29,770 P2
(45) Date of Patent: Oct. 23, 2018

(54) ***RHODODENDRON* PLANT NAMED 'ROBLEZA'**

(50) Latin Name: *Rhododendron hybrida*
Varietal Denomination: ROBLEZA

(71) Applicant: Robert Edward Lee, Independence, LA (US)

(72) Inventor: Robert Edward Lee, Independence, LA (US)

(73) Assignee: Plant Development Services, Inc., Loxley, AL (US)

( * ) Notice: Subject to any disclaimer, the term of this patent is extended or adjusted under 35 U.S.C. 154(b) by 0 days.

(21) Appl. No.: 15/732,124

(22) Filed: Sep. 19, 2017

(51) Int. Cl.
*A01H 5/00* (2018.01)

(52) U.S. Cl.
USPC ..... Plt./240

(58) Field of Classification Search
USPC ..... Plt./240
See application file for complete search history.

*Primary Examiner* — Annette H Para
(74) *Attorney, Agent, or Firm* — Cassandra Bright

(57) ABSTRACT

A new and distinct *Rhododendron* cultivar named 'ROBLEZA' is disclosed, characterized by upright fast growing, compact plants. Flowers are clear, bright red and occur as either single or double forms on the plant. Plants bloom Spring, Summer and Fall and exhibit good tolerance for both hot and cold conditions. The new cultivar is a *Rhododendron*, suitable for ornamental garden purposes.

2 Drawing Sheets

Figure 1:
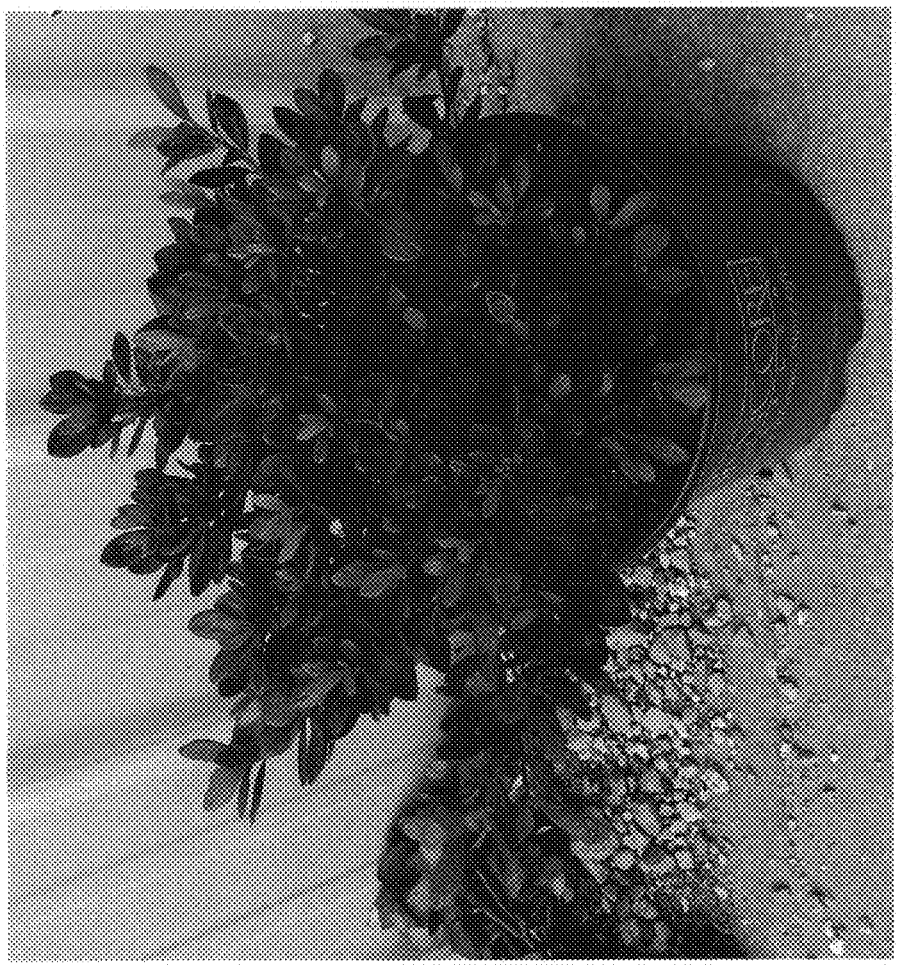

Latin name of the genus and species: *Rhododendron hybrida.*

Variety denomination: 'ROBLEZA'.

BACKGROUND OF THE INVENTION

The new cultivar is a product of a planned breeding program by the inventor, Robert Edward Lee. The inventor's intention was to develop *Rhododendron* hybrid plants with re-blooming characteristics. This new variety, hereinafter referred to as 'ROBLEZA', was discovered as a seedling, resulting from the crossing of *Rhododendron* 'Red Slipper', unpatented with the pollen parent *Rhododendron* 'Arabesk', unpatented. The cross resulting in the new variety occurred during 2004. The new variety was selected by the inventor during November of 2007 at a commercial nursery in Independence, La.

After identifying the new variety as a potentially interesting selection, the inventor first organized propagation of 'ROBLEZA' by vegetative cuttings Fall of 2007 at the same commercial nursery in Independence, La. The inventor continued controlled testing and propagation, assessing stability of the unique characteristics of this variety. Multiple generations have been reproduced and have shown that the unique features of this cultivar are stable and reproduced true to type.

SUMMARY OF THE INVENTION

The cultivar 'ROBLEZA' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'ROBLEZA' These characteristics in combination distinguish 'ROBLEZA' as a new and distinct *Rhododendron* cultivar:

1. Unique Spring, Summer, and Fall blooming.
2. Clear red flowers.
3. Upright growth habit.
4. Tolerant of both warm and cold environmental conditions.
5. Single and semi-double flower forms both present on plant.
6. Very good foundation plant.
7. Hardy to Zone 6.
8. Uniform, globular plant shape.

COMPARISON TO PARENT VARIETY

'ROBLEZA' is similar in most horticultural characteristics to the seed parent *Rhododendron* hybrid 'Red Slipper'. Plants of the new cultivar 'ROBLEZA' however differ in the following:

1. The new variety has a clearer red flower.
2. The new variety blooms more consistently over three seasons.
3. Plants of the new variety are more compact.

'ROBLEZA' is similar in most horticultural characteristics to the pollen parent *Rhododendron* hybrid 'Arabesk'. Plants of the new cultivar 'ROBLEZA' however differ in the following:

1. 'ROBLEZA' produces single and semi-double flowers, flowers of 'Arabesk' are always single.
2. The new variety has a brighter red flower.
3. The new variety blooms more consistently over three seasons.

COMMERCIAL COMPARISON

'ROBLEZA' can be compared to the commercial variety *Rhododendron* hybrid 'Conlef' U.S. Plant Pat. No. 10,579. Plants of the new cultivar 'ROBLEZA' are similar to plants of 'Conlef' in most horticultural characteristics, however, plants of the new cultivar 'ROBLEZA' differ in the following:

1. 'Robleza' has red flowers, 'Conlef' has red/pink flowers.
2. Plants of 'Robleza' are more compact than plants of 'Conlef'.

'ROBLEZA' can be compared to the commercial variety *Rhododendron* hybrid 'Roblez' U.S. Plant Pat. No. 28,279. Plants of the new cultivar 'ROBLEZA' are similar to plants of 'Roblez' in most horticultural characteristics, however, plants of the new cultivar 'ROBLEZA' differ in the following;

1. 'Robleza' has lighter red flowers than 'Roblez'.
2. Plants of 'Robleza' are more upright than plants of 'Roblez'.
3. Foliage of 'Robleza' is consistently green in the Winter, foliage of 'Roblez' can turn bronze in Winter.
4. Flower form of the new variety is single, flower form of Robleza is semi-double.

BRIEF DESCRIPTION OF THE PHOTOGRAPHS

The accompanying photograph in FIG. 1 illustrates in full color a typical plant of 'Robleza' in a 3 gallon pot.

Figure 2:
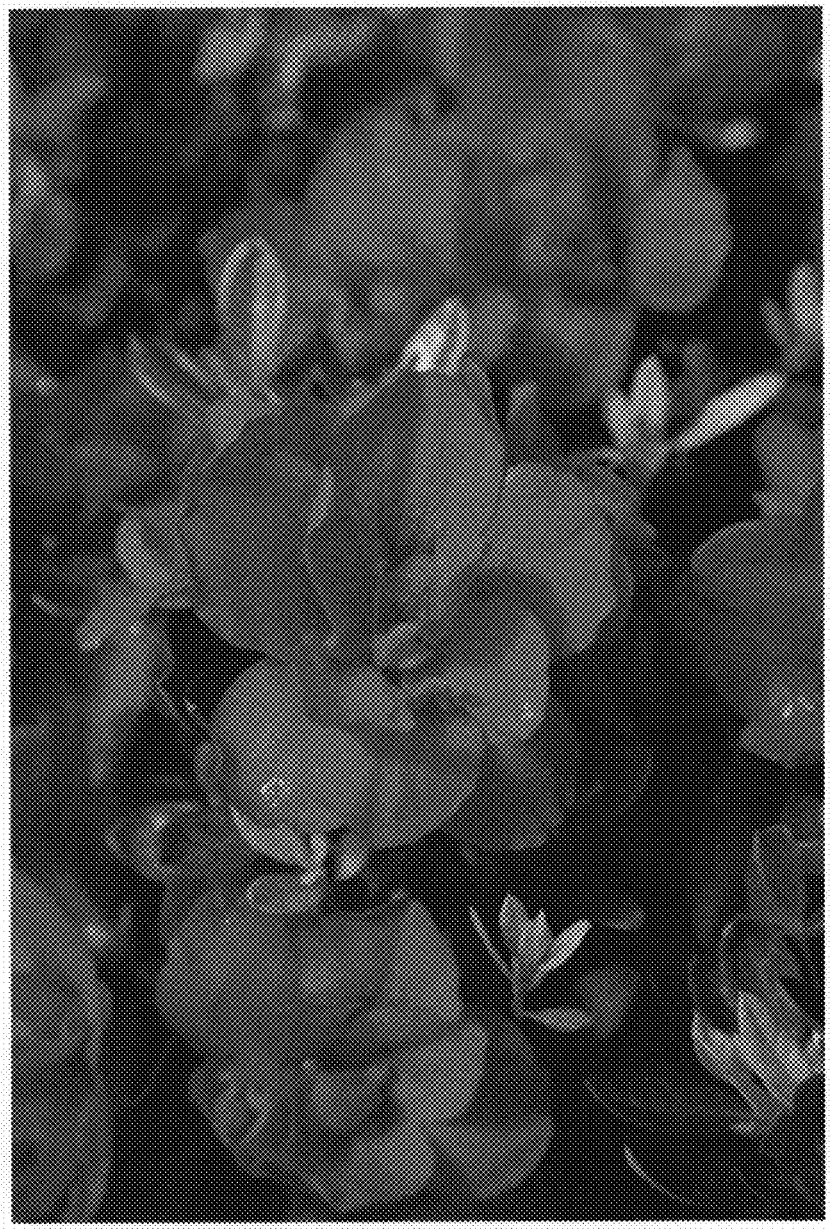

FIG. 2 illustrates a close up of typical flowers of the new variety.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'ROBLEZA' plants grown outdoors in Loxley, Ala. Plants are approximately 2 years old, in a 3 gallon nursery container. Measurements and numerical values represent averages of typical plant types.

Botanical classification: *Rhododendron hybrida* 'ROBLEZA'.

PROPAGATION

Typically by semi-hardwood cuttings in Spring and Summer.

Root description: Fine, fibrous young roots, well branched. Colored near RHS Grey-Brown 199A.

PLANT

Growth habit: Compact, upright, globular shrub.

Height: Approximately 45 cm to top of foliar and flowering plane.

Growth rate: Rapid.

Plant spread: Approximately 45 cm.

Branching characteristics: Well branched, approximately 4 to 5 primary branches from the center of the plant. Branches occur at approximately 15° to 45° angles. Each primary branch has 4 to 8 lateral branches.

Primary branches:

Length of primary branches: Average 19 cm.

Diameter of primary branches: Approximately 0.6 cm.

Primary branch strength: Very strong, flexible and difficult to break.

Primary branch color: Young primary branches near RHS Yellow-Green 144C; oldest branches become woody, colored near Brown 200B.

Primary branch texture: Immature growth hirsute. Older growth scaly, hirsute.

Lateral branches:

Number of lateral branches: Approximately 4 to 8 per primary branch.

Length of lateral branches: Average 9 cm.

Diameter of lateral branches: Average 0.4 cm.

Lateral branch strength: Very strong, flexible.

Lateral branch color: Immature branches near RHS Greyed-Red 180A, turning, Yellow-Green 144C.

Lateral branch texture: Hirsute.

Internode length: Average 1.0 to 1.5 cm.

Age of plant described: Approximately 2 years.

FOLIAGE

Leaf:

*Type*.—Simple.

*Arrangement*.—Alternate.

*Average length*.—Average range 3.5 to 4.8 cm.

*Average width*.—Average range 2.1 to 2.7 cm.

*Shape of blade*.—Obovate.

*Apex*.—Mucronate.

*Base*.—Broad attenuate.

*Attachment*.—Stalked.

*Margin*.—Entire.

*Texture of top surface*.—Pubescent. Hairs appressed.

*Texture of bottom surface*.—Pubescent. More hairs present along main vein and margin.

*Color*.—Young foliage upper side: Near RHS Yellow-Green 144B. Young foliage under side: Near RHS Yellow-Green 144C. Mature foliage upper side: Near RHS Green 139A. Mature foliage under side: Near RHS Green 137D.

*Venation*.—Type: Pinnate. Venation color upper side: Near RHS Yellow-Green N144A. Venation color under side: Near RHS Green 138B.

*Petiole*.—Length: About 0.6 cm. Diameter: About 0.15 cm. Color: Upper Surface: Near RHS Yellow-Green 144D. Lower Surface: Near RHS Yellow-Green N144D.

FLOWER

Bloom period: Plants begin flowering in the Spring, and continue to produce flowers throughout Summer and Fall.

Flower:

*Arrangement*.—Axillary clusters of single or semi-double, perfect, open funnel shaped individual flowers. Typically 3 to 5 flowers per cluster.

Inflorescence:

*Height*.—Average 12.0 cm.

*Diameter*.—Average 14.0 cm.

Peduncle:

*Length*.—Average range 4 to 7 cm.

*Diameter*.—0.3 cm.

*Color*.—Near RHS Yellow-Green 144C.

*Texture*.—Densely pubescent.

*Aspect*.—Straight. Angle of attachment, approximately 15 to 35° angle from stem.

Flowers:
*Length*.—Average 4.8 cm.
*Diameter*.—Average 6.2 cm.
*Facing direction*.—Outwardly and upwardly facing.
*Persistent or self-cleaning*.—Petals self-cleaning.
*Fragrance*.—Very faint.

Tube:
*Tube length*.—Approximately 1.7 cm.
*Tube width a widest point*.—Approximately 1.3 cm.
*Tube width and narrowest point*.—Approximately 0.5 cm.

Petals:
*Unfused petal segments*.—
*Length*.—Approximately 2.9 cm.
*Width*.—Approximately 3.7 cm
*Apex*.—Blunt, rounded with shallow, irregular lobes.
*Shape of petal*.—Unfused portion, obovate.
*Petal margin*.—Entire. Aspect very slightly undulating.
*Petal arrangement*.—Overlapping, bilateral symmetry dissecting bottom petal. Petals fused approximately ⅓ fused from base.
*Petal number*.—5, occasionally 3 to 5 petaloids present, forming a semi-double flower.
*Petal texture*.—Smooth.

Color:
*Upper surface at first opening*.—Near RHS Red 45C.
*Under surface at first opening*.—Near RHS Red 45C.
*Inner surface at maturity*.—Near RHS Red 45B, 3 upper petals dotted with Red 53A.
*Outer surface at maturity*.—Near RHS Red 45C.
*Upper surface at fading*.—Near RHS Red 46C, 3 upper petals dotted with Red 53A.
*Under surface at fading*.—Near RHS Red 46C.

Bud:
*Shape*.—Elliptic.
*Length*.—3.5 cm.
*Diameter*.—1.4 cm.
*Color*.—Near RHS Red 45B.

Calyx/sepals:
*Quantity per flower*.—5 sepals.
*Shape*.—Narrow deltate.
*Length*.—0.9 cm.
*Width*.—0.4 cm.
*Apex*.—Acute.
*Base*.—Fused.
*Margin*.—Entire.
*Texture*.—Highly pubescent.
*Color*.—Inner Surface: Near RHS Yellow-Green 145A. Outer Surface: Near RHS Yellow-Green 145A.

REPRODUCTIVE ORGANS

Stamens:
*Number*.—5 full stamens, 5 staminoidal structures, approximately 50% of the size of the full stamens.
*Length*.—2.8 cm.
*Width*.—0.1 cm.
*Color*.—Near RHS Red-Purple 58B.
*Anthers*.—Length: Approximately 0.3 cm. Color: Near RHS Red 53A. Pollen: Not observed.

Pistil:
*Number*.—1.
*Length*.—4.9 cm.
*Style*.—Length: Average 3.9 cm. Color: Near RHS Red 53D.
*Stigma*.—Globular, colored near Red 46C.
*Ovary*.—Sericeous texture. Approximately 0.3 cm in diameter. Colored near Yellow-Green 145A.

OTHER CHARACTERISTICS

Disease and pest resistance: Not observed to be susceptible nor resistant to normal diseases and pests of *Rhododendron*.

Temperature tolerance: USDA Zone 6 though Zone 9.

Fruit/seed production: Not observed to date.

What is claimed is:

1. A new and distinct cultivar of *Rhododendron* plant named 'ROBLEZA' as herein illustrated and described.

* * * * *